United States Patent
Treppendahl et al.

(10) Patent No.: US 6,372,776 B2
(45) Date of Patent: *Apr. 16, 2002

(54) CRYSTALLINE(−)-3R,4R-TRANS-7-METHOXY-2,2-DIMETHYL-3-PHENYL-4-{4-[2-(PYRROLIDIN-1-YL)ETHOXY]PHENYL}CHROMANE, HYDROGEN MALEATE

(75) Inventors: Svend Treppendahl, Virum; Klaus Snej Jensen, Frederiksberg C; Scott Eugene McGraw, Stenløse, all of (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/093,105

(22) Filed: Jun. 8, 1998

Related U.S. Application Data

(60) Provisional application No. 60/050,192, filed on Jun. 19, 1997.

(30) Foreign Application Priority Data

Jun. 12, 1997 (DK) ................................................ 0692/97

(51) Int. Cl.$^7$ .................... A61K 31/4025; C07D 405/10
(52) U.S. Cl. ........................................ 514/422; 548/525
(58) Field of Search ............................ 548/525; 514/422

(56) References Cited

U.S. PATENT DOCUMENTS

| | | | | |
|---|---|---|---|---|
| 4,093,631 A | * | 6/1978 | Gardner ....................... | 549/406 |
| 4,447,622 A | * | 5/1984 | Salman et al. ............... | 548/525 |
| 5,453,442 A | * | 9/1995 | Bryant et al. ................ | 514/408 |
| 5,464,862 A | * | 11/1995 | Labroo et al. ............... | 514/422 |

\* cited by examiner

Primary Examiner—T. A. Solola
(74) Attorney, Agent, or Firm—Reza Green, Esq.; Cheryl H. Agris, Esq.

(57) ABSTRACT

The present invention provides novel crystalline (−)-3R,4R-trans-7-methoxy-2,2-dimethyl-3-phenyl-4-{4-[2-(pyrrolidin-1-yl)ethoxy]phenyl}chromane, hydrogen maleate useful for reducing or preventing bone loss as well as pharmaceutical compositions containing the same. A process for preparing (−)-3R,4R-trans-7-methoxy-2,2-dimethyl-3-phenyl-4-{4-[2-(pyrrolidin-1-yl)ethoxy]phenyl}chromane, hydrogen maleate is described.

6 Claims, No Drawings

CRYSTALLINE(−)-3R,4R-TRANS-7-METHOXY-2,2-DIMETHYL-3-PHENYL-4-{4-[2-(PYRROLIDIN-1-YL)ETHOXY]PHENYL}CHROMANE, HYDROGEN MALEATE

CROSS-REFERENCE TO RELATED APPLICATIONS

This application claims the benefit of U.S. provisional application No. 60/050,192 filed on Jun. 19, 1997 the contents of which are fully incorporated herein by reference.

FIELD OF THE INVENTION

This invention relates to crystalline (−)-3R,4R-trans-7-methoxy-2,2-dimethyl-3-phenyl-4-{4-[2-(pyrrolidin-1-yl)ethoxy]phenyl}chromane, hydrogen maleate herein referred to as levormeloxifene maleate, its preparation and use as therapeutic agent.

BACKGROUND OF THE INVENTION

U.S. Pat. No. 5,280,040 and U.S. Pat. No. 5,464,862 discloses a class of 3,4-diarylchromans and their salts useful for reducing bone loss. U.S. Pat. No. 5,453,442 describes methods of lowering serum cholesterol and inhibiting smooth muscle cell proliferation in humans and inhibiting uterine fibroid disease and endometriosis in women by administering compounds of formula I as shown therein.

The preparation of 3,4-trans diarylchromanes is described in U.S. Pat. No. 3,822,287 and by Suprabhat Ray et al. in J. Med. Chem. 19, 276 (1976), the contents of which are incorporated herein by reference. The resolution of (+/−)-3,4-trans-7-methoxy-2,2-dimethyl-3-phenyl-4-{4-[2-(pyrrolidin-1-yl)ethoxy]phenyl}chromane in its optical antipodes is described in U.S. Pat. No. 4,447,622 incorporated herein by reference. Example 1 describes the preparation of the minus enantiomer, shown by formula I:

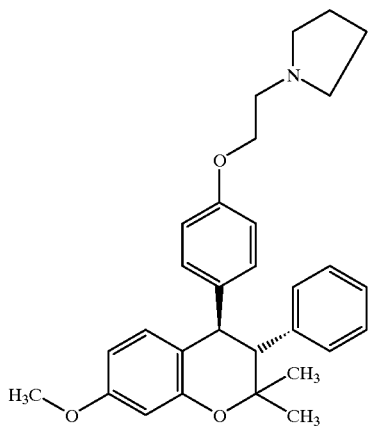

(I)

(In this specification the compound of formula I is referred to as levormeloxifene.)

In example 2 of U.S. Pat. No. 4,447,622 levormeloxifene is obtained as the free base and the hydrochloride salt.

However, the free base has a very poor solubility in water and the hydrochloride salt has some pharmaceutically undesirable properties. The hydrochloride salt is hygroscopic, it is quite heavy soluble in water and it forms a solid gel in aqueous suspension.

For commercial use it is important to have a physiologically acceptable salt with good stability, non-hygroscopicity, good bioavailability, good handling properties, and a reproducible crystalline form.

SUMMARY OF THE INVENTION

Within one aspect, the present invention provides crystalline (−)-3R,4R-trans-7-methoxy-2,2-dimethyl-3-phenyl-4-{4-[2-(pyrrolidin-1-yl)ethoxy]phenyl}chromane, hydrogen maleate.

Within another aspect of the invention there is provided a pharmaceutical composition comprising crystalline (−)-3R,4R-trans-7-methoxy-2,2-dimethyl-3-phenyl-4-{4-[2-(pyrrolidin-1-yl)ethoxy]phenyl}chromane, hydrogen maleate optionally in combination with a pharmaceutically acceptable carrier or diluent.

Within another aspect of the invention there is provided a process for the preparation of crystalline (−)-3R,4R-trans-7-methoxy-2,2-dimethyl-3-phenyl-4-{4-[2-(pyrrolidin-1-yl)ethoxy]phenyl}chromane, hydrogen maleate, which process comprises dissolving maleic acid and (−)-3R,4R-trans-7-methoxy-2,2-dimethyl-3-phenyl-4-{4-[2-(pyrrolidin-1-yl)ethoxy]phenyl}chromane in a common solvent, and crystallizing the resulting salt from the solution.

Within another aspect of the present invention there is provided a method of using the compound according to the invention to prevent or reduce bone loss.

DETAILED DESCRIPTION OF THE INVENTION

It has now been discovered that crystalline (−)-3R,4R-trans-7-methoxy-2,2-dimethyl-3-phenyl-4-{4-[2-(pyrrolidin-1-yl)ethoxy]phenyl}chromane, hydrogen maleate has the above described desired properties. In contrast to the hydrochloride salt, which is very hygroscopic, the hydrogen maleate salt is non-hygroscopic. Furthermore the hydrogen maleate salt has good stability characteristics, good bioavailability, good handling properties, and a reproducible crystalline form Accordingly, the present invention provides crystalline levormeloxifene maleate as a novel material, in particular in pharmaceutically acceptable form.

The present invention also provides a process for the preparation of crystalline (−)-3R,4R-trans-7-methoxy-2,2-dimethyl-3-phenyl-4-{4-[2-(pyrrolidin-1-yl)ethoxy]phenyl}chromane, hydrogen maleate, which process comprises dissolving maleic acid and (−)-3R,4R-trans-7-methoxy-2,2-dimethyl-3-phenyl-4-{4-[2-(pyrrolidin-1-yl)ethoxy]phenyl}chromane in a common solvent, and crystallizing the resulting salt from the solution.

Examples of the common solvents include but are not limited to organic solvents in particular lower aliphatic alcohol's such as ethanol, 2-propanol, 2-butanol, 1-hexanol and solvents like toluene, isobutylmethylketone and tetrahydrofuran. The mixture of the components are conveniently performed at temperatures from 40 to 60° C. before cooling down to 5° C. and collection of the crystals by filtration.

The present invention also provides a pharmaceutical composition comprising crystalline (−)-3R,4R-trans-7-methoxy-2,2-dimethyl-3-phenyl-4-{4-[2-(pyrrolidin-1-yl)ethoxy]phenyl}chromane, hydrogen maleate optionally together with a pharmaceutically acceptable carrier or diluent.

Crystalline (−)-3R,4R-trans-7-methoxy-2,2-dimethyl-3-phenyl-4-{4-[2-(pyrrolidin-1-yl)ethoxy]phenyl}chromane, hydrogen maleate may be used in human and veterinary medicine for the regulation of bone metabolism. The present invention provides thus according to another aspect a method of preventing or reducing bone loss in a mammal in need of such treatment or prevention comprising administering a therapeutically effective amount of the compound according to the invention. Levormeloxifene maleate may be used, for example, in the treatment of patients suffering from bone loss due to osteoporosis (including postmenopausal osteoporosis and glucocorticoid-related osteoporosis), Paget's disease, hyperparathyroidism, hypercalcemia of malignancy and other conditions characterized by excessive rates of bone resorption and/or decreased rates of bone formation or in patients susceptible to bone loss. Furthermore, the compound has effects on the cardiovascular system where it lowers serum cholesterol, inhibits lipid accumulation in the arterial wall, acts as a vasodilator and interferes with the coagulation process, wherefore it may be used for the prevention and treatment of, for example, atherosclerosis, hyperlipidemia and hypercoagulability. It may also be used, for example, in the treatment of female patients suffering from endometriosis, dysfunctional bleeding, endometrial cancer, polycystic ovarian syndrome, anovulatory bleeding and breast cancer and male patients with gynecomastia, prostate hypertrophy and prostate carcinoma. It may also be used to induce endometrial thinning prior to intrauterine surgery. Furthermore, it may be used, for example, to treat menopausal symptoms, and atrophy of mucous membranes and skin. The compound may be used, for example, in the treatment of patients suffering from obesity and Alzheimer's disease.

For use within the present invention, crystalline (−)-3R, 4R-trans-7-methoxy-2,2-dimethyl-3-phenyl-4-{4-[2-(pyrrolidin-1-yl)ethoxy]phenyl}chromane, hydrogen maleate may be formulated with a pharmaceutically acceptable carrier or excipient to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compound in an appropriate manner, and in accordance with accepted practices, such as those disclosed in *Remington's Pharmaceutical Sciences,* Gennaro, ed., Mack Publishing Co., Easton, Pa., 1990.

The compositions of this invention are usually adapted for oral administration, or as formulations for dissolution for parenteral administration. Oral administration is preferred.

For oral administration crystalline (−)-3R,4R-trans-7-methoxy-2,2-dimethyl-3-phenyl-4-{4-[2-(pyrrolidin-1-yl) ethoxy]phenyl}chromane, hydrogen maleate is prepared in a form suitable for oral administration, such as a tablet or capsule. Typically, the compound is combined with a carrier and molded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions are administered one or more times per day or week. An effective amount of such a pharmaceutical composition is the amount that provides a clinically significant effect. Such amounts will depend, in part, on the particular condition to be treated, age, weight, and general health of the patient, and other factors evident to those skilled in the art.

The pharmaceutical compositions may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., *J Pharm Sci* 73 (1964), 1294–1297, 1984; U.S. Pat. Nos. 4,489,056; and 4,210,644, which are incorporated herein by reference.

The composition is usually presented as a unit dose composition containing 0.1–1000 mg of a compound in accordance with the invention for oral dosing. Typical dosage for e.g. osteoporotic effect would vary between 0.1–500 mg, preferably between 0.1–280 mg per day either once or divided in 2 or 3 doses when administered orally or 2 or 3 times per week or once weekly or once per 14 days.

Preferred unit dosage forms include in solid form, tablets or capsules, in liquid form, solutions, suspensions, emulsions, elixirs or capsules filled with the same, or in form of sterile injectable solutions, or patches, vagitories, vaginal rings or long lasting implantates.

The composition of this invention may be formulated by conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohol's, polyethylene glycol's, polyhydroxyethoxylated castor oil, syrup, peanut oil, olive oil, gelatin, lactose, terra alba, sucrose, agar, pectin, acacia, amylose, magnesium stearate, talc, silicic acid, stearic acid, fatty acid monoglycerides and diglycerides, pentaerythritol fatty acid esters, hydroxymethylcellulose and polyvinylpyrrolidone and calcium phosphates.

The pharmaceutical preparations can be sterilized and mixed, if desired, with auxiliary agents, such as binders, lubricants, preservatives, disintegrants, stabilizers, wetting agents, emulsifiers, salt for influencing osmotic pressure, buffers and/or colouring substances and the like, which do not deleteriously react with the active compound.

For parenteral application, particularly suitable are injectable solutions or suspensions, preferably aqueous solutions with the active compound dissolved in polyhydroxylated castor oil.

For oral administration, particularly suitable are tablets, dragees, or capsules having talc and/or a carbohydrate carrier or binder or the like, the carrier preferably being lactose or calcium phosphate and/or corn starch and/or potato starch. A syrup, elixir or like can be used when a sweetened vehicle can be employed.

A typical tablet, which may be prepared by conventional tabletting techniques, contains:

| | |
|---|---|
| Active compound | 10 mg |
| Lactosum | 67.8 mg Ph. Eur. |
| Avicel ® | 31.4 mg |
| Talc | 1.0 mg |
| Magnesii stearas | 0.25 mg Ph. Eur. |

The present invention is further illustrated by the following examples which, however, are not to be construed as limiting the scope of protection. The features disclosed in the fore-going description and in the following examples may, both separately and in any combination thereof, be material for realising the invention in diverse forms thereof.

Levormeloxifene maleate was synthesized, purified and crystallized as described in the following example.

EXAMPLE 1

(−)-3R,4R-trans-7-methoxy-2,2-dimethyl-3-phenyl-4-{4-[2-(pyrrolidin-1-yl)ethoxy]phenyl}chromane, hydrogen maleate (levormeloxifene maleate)

To a stirred, 50° C. warm, solution of (+/−)-trans-7-methoxy-2,2-dimethyl-3-phenyl-4-{4-[2-(pyrrolidin-1-yl)ethoxy]phenyl}chromane (1.00 kg, 2.19 mol) in methanol (10 l) was added (+)-ditoluoyltartaric acid (464 g, 1.20 mol). The suspension was stirred at 50° C. until the solution was homogenous.

Formic acid (73 g, 1.59 mol) was added to the solution and the temperature was allowed to drop to 30–40° C. If the crystallization has not started at this point, the solution was seeded, and the temperature was allowed to drop further down to 20° C. The suspension was stirred for two hours at 20° C. and then cooled down to 5–10° C. for two hours and the crystals were collected by filtration. Yield 742 g.

Recrystallization from refluxing methanol (26 l) gave after cooling to 5–10° C. and filtration pure crystals of the levormeloxifene (+)-ditoluoyltartrate salt. Yield 556 g. M.p. 136–138° C. (dec.).

(−)-3R,4R-trans-7-methoxy-2,2-dimethyl-3-phenyl-4-{4-[2-(pyrrolidin-1-yl)ethoxy]phenyl}chromane, (+)-ditoluoyltartrate (500 g) was suspended in a mixture of toluene (2.5 l), water (2 l) and sodium carbonate (157 g) at ambient temperature. The mixture was stirred until the salts were dissolved. The aqueous phase was separated. The toluene phase was washed with water (2 l) and evaporated to an oil.

A part of the oil (3 g, 0.0066 mole) was dissolved in toluene (60 ml). Maleic acid (0.8 g, 0.0066 mole) was added. The mixture was heated until homogenous. It was stirred over night at ambient temperature. The maleinate salt crystallized readily. The title compound was collected by filtration and dried at 50° C. to give 3 g (80%).

The compound was identified by NMR and elemental analysis.

What is claimed is:

1. Crystalline (−)-3R,4R-trans-7-methoxy-2,2-dimethyl-3-phenyl-4-{4-[2-(pyrrolidin-1-yl)ethoxy]phenyl}chromane, hydrogen maleate.

2. A process for the preparation of crystalline(−)-3R,4R-trans-7-methoxy-2,2-dimethyl-3-phenyl-4-{4-[2-(pyrrolidin-1-yl)ethoxy]phenyl}chromane, hydrogen maleate of claim 1, which process comprises dissolving maleic acid and (−)-3R,4R-trans-7-methoxy-2,2-dimethyl-3-phenyl-4-{4-[2-(pyrrolidin-1-yl)ethoxy]phenyl}chromane in a common solvent, and crystallizing the resulting salt from the solution.

3. A pharmaceutical composition comprising the crystalline (−)-3R,4R-trans-7-methoxy-2,2-dimethyl-3-phenyl-4-{4-[2-(pyrrolidin-1-yl)ethoxy]phenyl}chromane, hydrogen maleate of claim 1 together with a pharmaceutically acceptable carrier or diluent.

4. The pharmaceutical composition of claim 3 in the form of a dosage unit containing about 0.1–280 mg per day.

5. A method for reducing or preventing bones loss comprising administering to a patient in need of such treatment or prevention an effective amount of a compound of claim 1.

6. The method of claim 5 wherein the bone loss is due to osteoporosis.

\* \* \* \* \*